United States Patent
Jones et al.

(10) Patent No.: US 7,869,038 B2
(45) Date of Patent: Jan. 11, 2011

(54) BROAD-RANGE SPECTROMETER

(75) Inventors: Lewis Jones, West Malvern (GB); Nigel Lightfoot, Malvern (GB); David Spriggs, Malvern (GB); David Stringfellow, Malvern (GB)

(73) Assignee: Malvern Instruments, Ltd., Malvern (GB)

( * ) Notice: Subject to any disclaimer, the term of this patent is extended or adjusted under 35 U.S.C. 154(b) by 314 days.

(21) Appl. No.: 12/228,871

(22) Filed: Aug. 15, 2008

(65) Prior Publication Data

US 2009/0122313 A1    May 14, 2009

Related U.S. Application Data

(60) Provisional application No. 60/964,828, filed on Aug. 15, 2007.

(51) Int. Cl.
  *G01N 15/02* (2006.01)
  *G01N 21/00* (2006.01)
(52) U.S. Cl. ................ 356/338; 356/335; 356/343
(58) Field of Classification Search .......... 356/32–35.5, 356/364–370, 616–617
  See application file for complete search history.

(56) References Cited

U.S. PATENT DOCUMENTS

| | | | | |
|---|---|---|---|---|
| 4,545,677 A | * | 10/1985 | Chupp | ........................ 356/39 |
| 4,755,052 A | | 7/1988 | Giglio et al. | |
| 4,953,978 A | | 9/1990 | Bott et al. | |
| 5,104,221 A | | 4/1992 | Bott et al. | |
| 5,164,787 A | * | 11/1992 | Igushi et al. | ................ 356/336 |
| 6,034,760 A | * | 3/2000 | Rees | .......................... 356/28.5 |
| 6,618,140 B2 | * | 9/2003 | Frost et al. | ................... 356/317 |
| 6,819,411 B1 | * | 11/2004 | Sharpe et al. | ................. 356/72 |
| 7,596,454 B2 | * | 9/2009 | Storz et al. | ..................... 702/27 |
| 2002/0036776 A1 | | 3/2002 | Shimaoka | |

FOREIGN PATENT DOCUMENTS

DE    10/2006/019138 A1    10/2007
JP    59160741    9/1984

OTHER PUBLICATIONS

A Laser Diagnostic Techniques for the Measurement of Droplet and Particle Size Distribution, J. Swithenback et al., University of Sheffield, England, 1977.

* cited by examiner

*Primary Examiner*—Gregory J Toatley
*Assistant Examiner*—Jarreas C Underwood
(74) *Attorney, Agent, or Firm*—Kristofer E. Elbing

(57) ABSTRACT

In one general aspect, a particle characterization instrument is disclosed that includes a first spatially coherent light source with a beam output aligned with an optical axis. A focusing optic is positioned along the optical axis after the coherent light source, and a sample cell is positioned along the optical axis after the focusing optic. The instrument also includes a diverging optic positioned along the optical axis after the sample cell, and a detector positioned outside of the optical axis to receive scattered light within a first range of scattering angles from the diverging optic. In another general aspect, an instrument can direct at least a portion of a first beam and at least a portion of a second beam along a same optical axis and a can receive scattered light from the sample cell resulting from interaction between the sample and either the first beam or the second beam.

35 Claims, 11 Drawing Sheets

BROAD-RANGE SPECTROMETER

CROSS-REFERENCE TO RELATED APPLICATION

This application claims the benefit under 35 U.S.C. 119(e) of U.S. provisional application Ser. No. 60/964,828 filed Aug. 15, 2007 which is herein incorporated by reference.

FIELD OF THE INVENTION

This invention relates generally to instruments made to detect scattered light from particles in order to determine their size.

BACKGROUND OF THE INVENTION

Light of a particular wavelength falling on particles will be scattered over a range of angles, determined by the size of the particle. The size of particles can thus be inferred by measuring the scattered light over a range of angles. This principle has been used as the basis of commercially-made instruments incorporating visible laser light source for measuring particles around 0.1 µm to 3000 µm in diameter.

1. Fourier Configuration

Referring to FIG. 1, in instances where bulk size distribution is required, it is convenient to pass a representative (usually large) number of particles through a static beam of light and to detect the light scattered onto a number of photodetectors of fixed size and position. The illuminating beam is preferably at least 10 times larger (in diameter) than the largest particle.

The particles scatter light within the volume in which they intersect the beam. The finite extent of this volume means that detectors simply placed around the cell will collect light from a range of angles, reducing the capability for discrimination of different particle sizes.

Referring to FIG. 2, instruments, such as ones that employ the Fourier configuration, can use segmented photodetector arrays. These provide multiple detector elements that allow different angles of light to be resolved.

2. Telephoto (Fourier)

Measurement of larger particles requires the detection of small angles close to the focused beam. This would appear to require either reducing the size of the photodetector elements nearest the beam, or by using a weaker focusing lens in order to increase the distance of the detector plane from the lens. Referring to FIG. 3, one sophistication that can be employed, when only low angles need to be measured, is to use a telephoto lens arrangement to shorten the physical distance whilst achieving the same effective focal length.

The focusing lens has a short focal length, with a concave lens placed slightly short of its focus, to expand the scattering angles. A limitation of this system is that it has not been readily feasible to produce an expanding lens form capable of collecting larger scattering angles without severe distortion. There is a range of angles that can be measured beyond the radial extent of the expanding lens but these will be discontinuous from the low angle detection range. Large angles can not be detected with the lens arrangement as shown.

2. Binocular Fourier (Coulter)

Referring to FIG. 4, the problem of measuring large angles simultaneously with small angles was overcome by a combination of two collecting lens systems, revealed by Beckman Coulter. A Fourier lens on axis is truncated in one side to allow unobscured detection of higher angles on that side, whilst intermediate angles are detected on the opposite side of the axis. For a given minimum detector spacing, this scheme has a longer track length, since the effective focal length is the distance between the axial lens and the detector plane, and there is additional distance between the cell and the axial length to allow for the detection of higher angles.

3. Reverse Fourier

Referring to FIG. 5, the track length can be reduced using the so-called reverse Fourier configuration in which the focusing lens is in front of the sample. The effective focal length of this system is the distance between the sample and the detection plane. This allows continuous measurement from small to large forward angles. So long as they are placed in the focal plane of the lens, there is no need for any more lenses on the detectors. For large forward angle detection, it is useful to put lenses in front of individual detector elements in order to increase the light gathering area without having to use large detectors. With appropriately designed lens and aperture on these channels it possible to place these detectors closer to the sample than the focal plane. Backscatter can also be measured if the focusing lens is set a reasonable distance back from the measurement volume.

SUMMARY OF THE INVENTION

In one general aspect, the invention features a particle characterization instrument that includes a first spatially coherent light source with a beam output aligned with an optical axis. A focusing optic is positioned along the optical axis after the coherent light source, and a sample cell is positioned along the optical axis after the focusing optic. The instrument also includes a diverging optic positioned along the optical axis after the sample cell, and a detector positioned outside of the optical axis to receive scattered light within a first range of scattering angles from the diverging optic.

In preferred embodiments, the apparatus can further include a second light source having a wavelength that is different from a wavelength of the first light source. The wavelength of the first source can be longer than the wavelength of the second source, and the different wavelengths can provide an increased dynamic range to the instrument. The first wavelength can be a wavelength in the spectral vicinity of red and the second wavelength can be a wavelength in the spectral vicinity of violet. The apparatus can further include a second detector positioned outside the optical axis to receive further scattered light within a second range of scattering angles that are sufficiently large to cause it to pass outside of the diverging optic. The diverging optic can be a lens having at least one concave refractive surface. The apparatus can further include a second light source having a wavelength that is different from a wavelength of the first light source. The wavelength of the first source can be longer than the wavelength of the second source, and the different wavelengths can provide an increased dynamic range to the instrument. The apparatus can further include a second detector positioned outside the optical axis to receive further scattered light within a second range of scattering angles that are sufficiently large to cause it to pass outside of the diverging optic. The concave refractive surface can be a refractive portion of a circular concave surface and a portion of the circular concave surface can be truncated to allow scattered light to pass through unrefracted. The apparatus can further include a second detector positioned outside the optical axis to receive further scattered light within a second range of scattering angles after it passes through the truncated portion of the circular concave surface. The apparatus can further include a third detector positioned outside the optical axis to receive further scattered light within a third range of scattering angles that are sufficiently large to cause it to pass outside of the diverging optic. The apparatus can further include a second light source having a wavelength that is different from a wavelength of the first light source. The diverging optic can include a convex reflective surface. The diverging optic in which the reflecting surface can be a reflecting portion of a circular convex surface and a portion of the circular convex surface can be truncated to allow scattered light to pass through unreflected. The apparatus can further include a second detector positioned outside the optical axis to receive further scattered light within a second range of scattering angles after it passes through the truncated portion of the circular convex surface. The apparatus can further include a third detector positioned outside the optical axis to receive further scattered light within a third range of scattering angles that are sufficiently large to cause it to pass outside of the diverging optic. The apparatus can further include a second light source having a wavelength that is different from a wavelength of the first light source, the divergent optic can be dichroic to reflect light from the first source while allowing light from the second source to pass through, and the apparatus can further include a second detector behind the divergent optic to receive scattered light from the second source. The apparatus can further include a third detector positioned outside the optical axis to receive further scattered light from the second wavelength within a third range of scattering angles that are sufficiently large to pass outside of the diverging optic. The apparatus can further include a mirror between the light source and the focusing optic that bends the optical axis. The apparatus can further include a second light source having a wavelength that is different from a wavelength of the first light source, and the mirror can be dichroic to reflect light from the first source while allowing light from the second source to pass through. The first wavelength can be a red wavelength and the second wavelength can be a violet wavelength. The source can be a solid-state source. The apparatus can further include at least one backscatter detector positioned outside of the optical axis behind the sample cell. The apparatus can further include a second light source having a wavelength that is different from a wavelength of the first light source. The apparatus can further include a second detector positioned outside the optical axis to receive further scattered light within a second range of scattering angles that are sufficiently large to cause it to pass outside of the diverging optic. The first and second detectors can be multi-element detectors.

In another general aspect, the invention features a particle characterization method that includes shining a beam of spatially coherent light, focusing the beam of light to produce a focused beam of light, causing the focused beam of light to interact with a plurality of particles to produce scattered light, spreading at least a portion of the scattered light resulting from the interaction between the focused beam and the particles to produce a spread scattered light beam, and detecting at least part of the spread scattered light beam.

In a further general aspect, the invention features a particle characterization instrument that includes means for shining a beam of spatially coherent light, means for focusing the beam of light to produce a focused beam of light, means for causing the focused beam of light to interact with a constrained plurality of particles to produce scattered light, means for spreading at least a portion of the scattered light resulting from the interaction between the focused beam and the particles to produce a spread scattered light beam, and means for detecting at least part of the spread scattered light beam.

In another general aspect, the invention features a particle characterization instrument that includes a first spatially coherent light source having a first wavelength and a first beam output, a second light source having a second wavelength that is different from the first wavelength and having a second beam output, a first optical combiner responsive to the first beam output and to the second beam output and being positioned to direct at least a portion of a first output beam from the first beam output and at least a portion of a second output beam from the second beam output along a same optical axis, a sample cell positioned along the same optical axis such that it can receive the first output beam or the second output beam as they are the directed along the same optical axis, and a first detector positioned outside of the optical axis to receive scattered light from the sample cell resulting from interaction between the sample and either the first output beam or the second outlet beam.

In preferred embodiments the optical combiner can be a dichroic mirror. The instrument can further include another mirror, with the dichroic mirror redirecting at least a portion of the first output beam along the optical axis and the other mirror redirecting at least a portion of the second output beam along the optical axis. The instrument can further include a first detector positioned to receive at least a portion of the first output beam and a second detector positioned to receive at least a portion of the second output beam. The optical combiner can be positioned to allow full overlap of the beams. The second light source can be a spatially coherent light source.

In a further general aspect, the invention features a particle characterization method that includes shining a first beam of spatially coherent light having a first wavelength, shining a second beam of light having a second wavelength, directing at least one of the first and second beams of light to cause them to shine along a same optical axis, causing the first directed beam of light to interact with a sample including plurality of particles in the optical axis to produce scattered light, detecting the scattered light from the first beam, causing the second directed beam of light to interact with the sample in the optical axis to produce more scattered light, and detecting the scattered light from the second beam.

In preferred embodiments the step of directing can be a two-part step that redirects the first and second beams of light. The step of shining a second beam of light can shine spatially coherent light. The step of shining a first beam and the step of detecting scattered light from the first beam can occur before the step of shining a second beam.

In another general aspect, the invention features a particle characterization instrument that includes means for shining a first beam of spatially coherent light having a first wavelength, means for shining a second beam of spatially coherent light having a second wavelength, means for directing at least one of the first and second beams of light to cause them to shine along a same optical axis, means for causing the first directed beam of light to interact with a sample including a plurality of particles in the optical axis to produce scattered light, and for causing the second directed beam of light to interact with the sample in the optical axis to produce more scattered light, and means for detecting the scattered light from the first beam and the second beam.

Instruments according to the invention can allow the detection of highly resolved forward angles and large forward and backward angles on the same configuration of hardware without having to use impractically small detector elements or a long optical track. This can be done by using adding a diverging optic, such as a negative lens, to a reverse Fourier configuration to magnify small angles near the focused beam. Instruments according to the invention can also be beneficial in that they can provide high quality measurements over a broad wavelength range, such as through the use of dual sources.

DESCRIPTION OF AN ILLUSTRATIVE EMBODIMENT

Figure 6B:
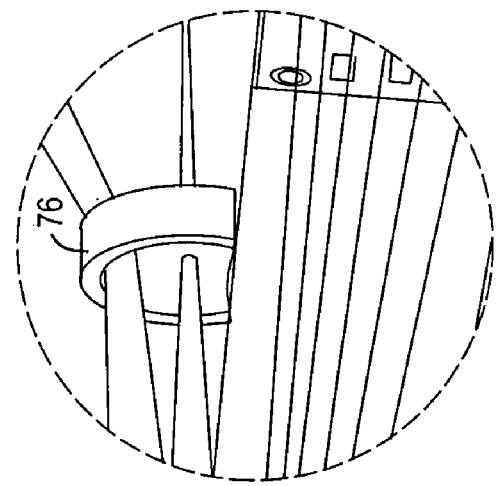
FIG. 6 is a perspective diagram of an illustrative particle size measurement instrument according to the invention that employs a diverging lens.
Figure 6A:
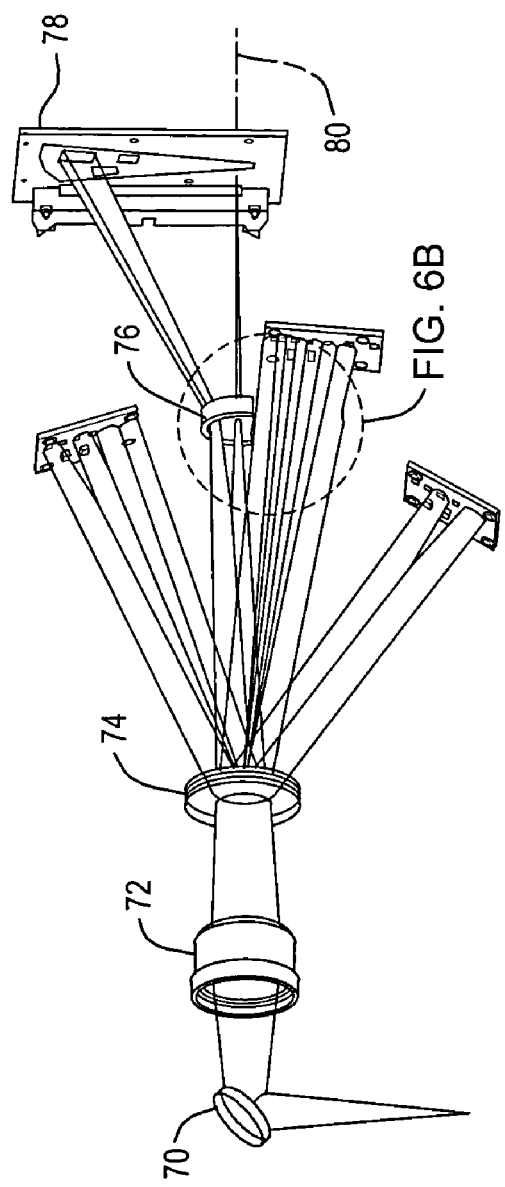
Figure 7:
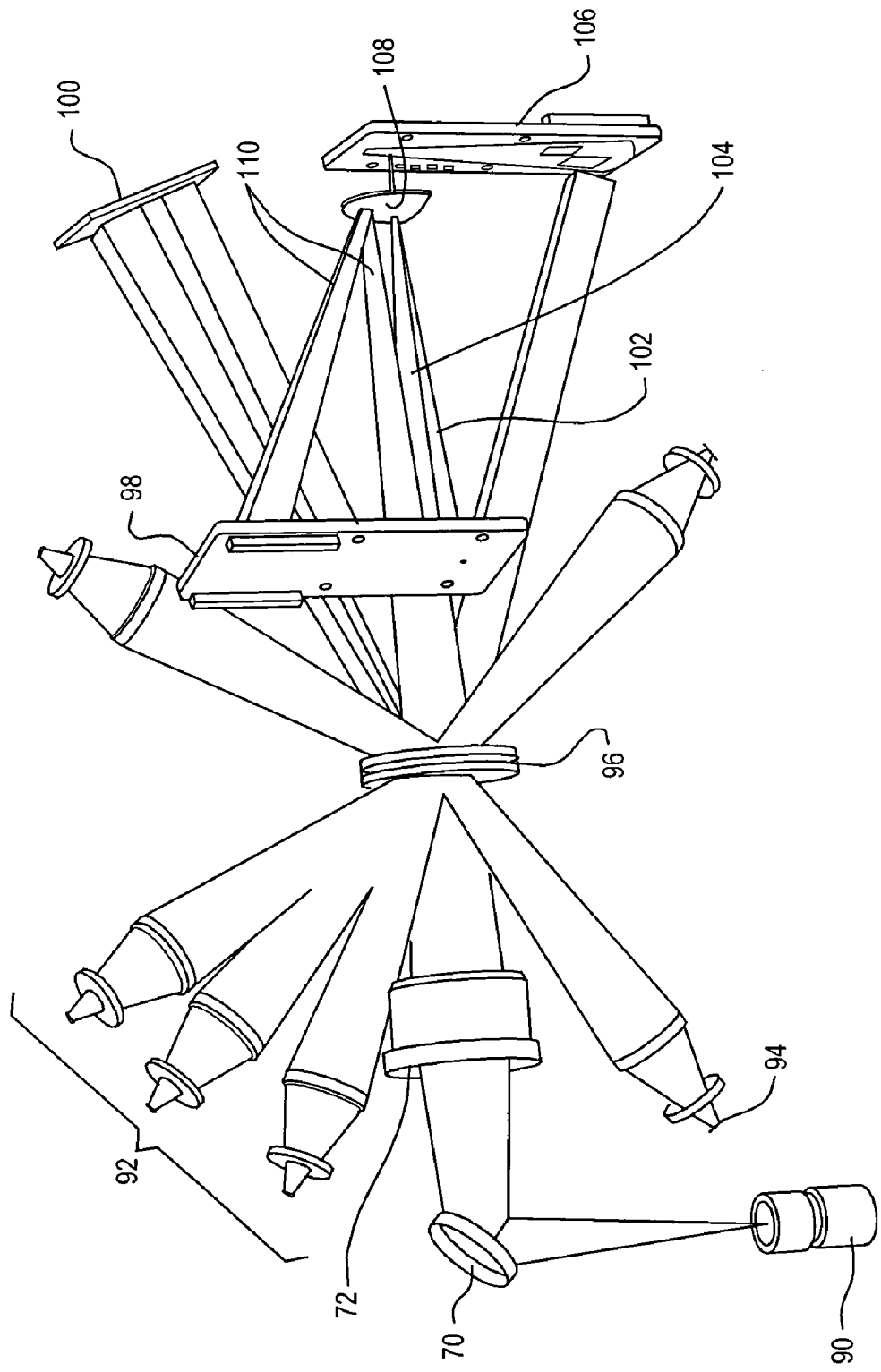
FIG. 7 is a perspective diagram of an illustrative particle size measurement instrument according to the invention that employs a diverging mirror.

Referring to FIGS. 6 and 7, one preferred embodiment of this invention involves a few added features, so as to make the instrument capable of measuring a large range of sample sizes whilst fitting into a small space. Red light from a laser diode is focused through a pinhole to remove aberrations and stray light from the source. It is then reflected into the instrument optical axis using a planar mirror 70. A small but fixed proportion of light passes through the dichroic coating to a photodetector that is used to monitor or control the output of the laser source.

The main beam continues to expand until it reaches a focusing lens system 72 beyond which it converges to a $1/\epsilon^2$ diameter of 10 mm at a flow cell 50 mm away (74). The unscattered light continues to converge towards a focus until it hits a diverging lens 76 (FIG. 6) or a convex blue-pass dichroic mirror 108 (FIG. 7), cut down on one side to allow scattering angles of 3.7° or more to pass on one side towards an array of photodetectors 78 in the focal plane. The curved mirror is tilted in the plane perpendicular to the optical axis 80 and the scatter detection to cause the reflected beam to be focused onto another focal plane detector. This mirror also reflects low angle scattered light onto the second detector array. Angles up to 1.7° can be detected above or below the focused beam, since the lens is truncated 5 mm below its centre; angles up to 4° can be detected horizontally or upwards. Detection of angles between 4° and 7.6 must be downwards, to avoid the reflecting lens. Forward angles from 7.6° up to the cell limits can be detected at any orientation that is not obscured by the low angle focal plane detector. In the preferred embodiment, these larger forward angles are detected upwards with one array of sidescatter detectors and two or three more individually lensed detectors for the high angles, above and below the focused beam.

The effective focal length of this scheme is many times longer than the track length of the system. In the preferred embodiment, the numerical aperture of the beam focused on the detector is equivalent to a 900 mm distance from cell to detector, and yet the whole optical train is shorter than 300 mm.

In one embodiment, distance of first surface of first lens from 658 nm light source of 0.905 numerical aperture is 128.6 mm The first lens is made of N-BK7 glass and has centre thickness of 5.0 mm with radii of −102.3 mm and −41.3 mm respectively.

The second lens is a cemented doublet placed with an air gap of 1.0 mm from the first along the optical axis. The radius of curvature of the first surface is 115.2; the centreline thickness is 2.5 mm and the material is N-LASF44 glass.

The radius of curvature of the interface surface is 35.8 mm. The second component of the doublet is N-BK7 glass and has a centre thickness of 8 mm and an exit curvature of −93.8 mm. These components form a module depicted as item 72 of FIG. 6A. The flow cell is 50 mm away, has two N-BK7 windows 3 mm thick and a water gap of 2.2 mm, depicted as item 73 of FIG. 6A.

The negative lens is made of N-LASF44 and is depicted as item 76 of FIGS. 6A&B. Its first radius of curvature is −22.1 mm and is 139.2 mm away from the flow cell exit face. Its centre thickness is 2.5 mm and its second face has a radius of curvature of 70.4 mm. It is has a chordal cut 5 mm to one side of the central axis.

The focal Plane detector array is 95.5 mm from the exit face of the negative lens and is depicted as item 78 of FIG. 6A. It has a pinhole diameter of 0.1 mm which is positioned to allow passage of the focused beam. The focal plane photodetector array has 38 photosensitive elements arranged predominantly on one side at distances from 0.08 mm to 65.3 mm with an expansion ratio between subsequent detectors of approximately 20%.

Sidescatter detectors placed close to the cut side of the expanding lens will be able to measure scattering angles as low as 4 degrees which is well within the range that can be measured by the outer detectors on the focal plane.

Referring also to FIG. 7, an illustrative particle size measurement instrument according to the invention can also employ a diverging mirror 108. In this type of embodiment, low angle scattered light 110 is reflected back to a low-angle focal plane detector 104. This arrangement allows the instrument to be even shorter. Mirror-based embodiments can be similar in other respects to lens-based embodiments.

Detectors can be placed so as to collect light in more than one scatter plane if there is a requirement to collect information on shape or orientation of particles.

Figure 8:
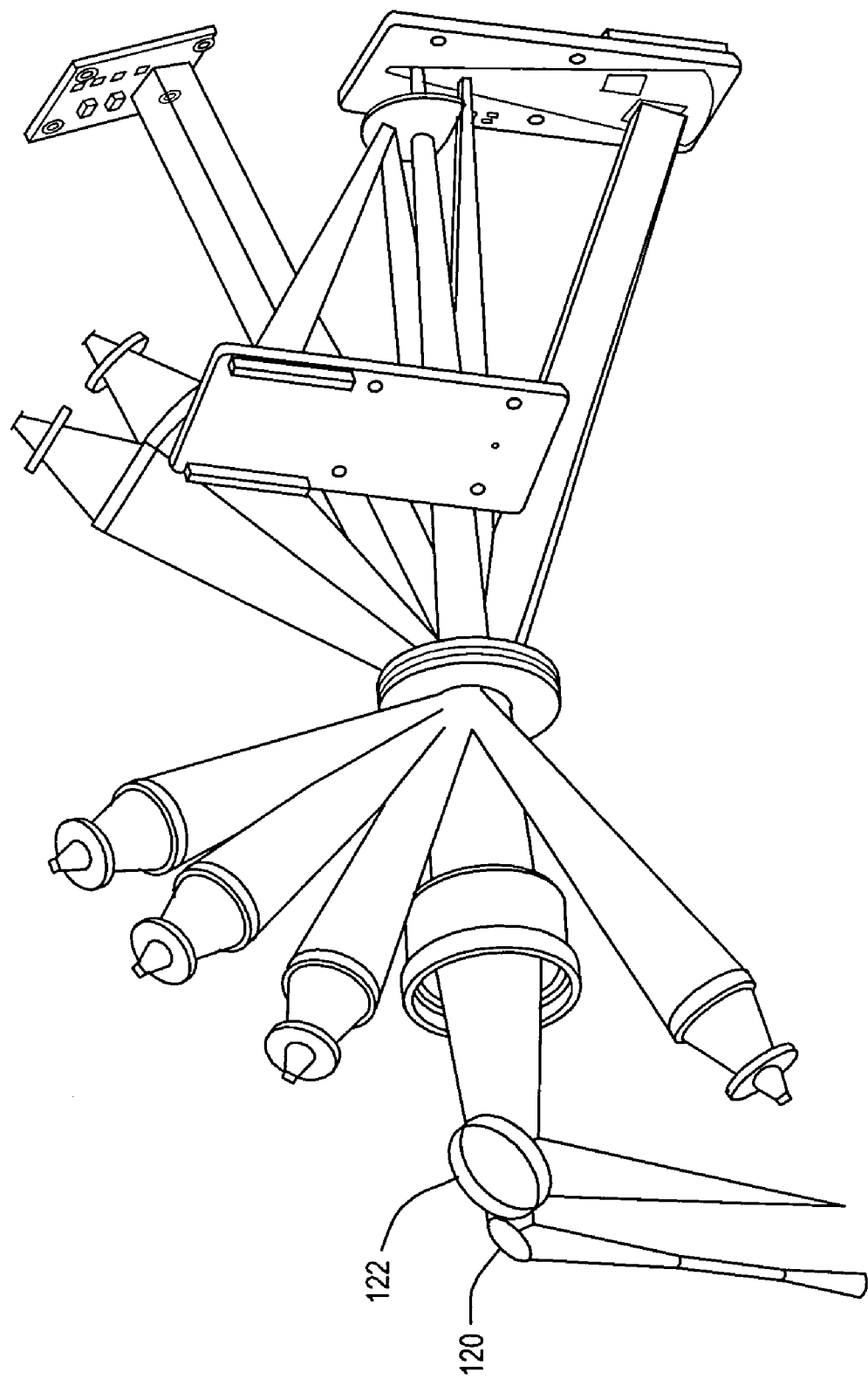
FIG. 8 is a perspective diagram of an illustrative particle size measurement instrument according to the invention that employs two wavelengths.
Figure 9:
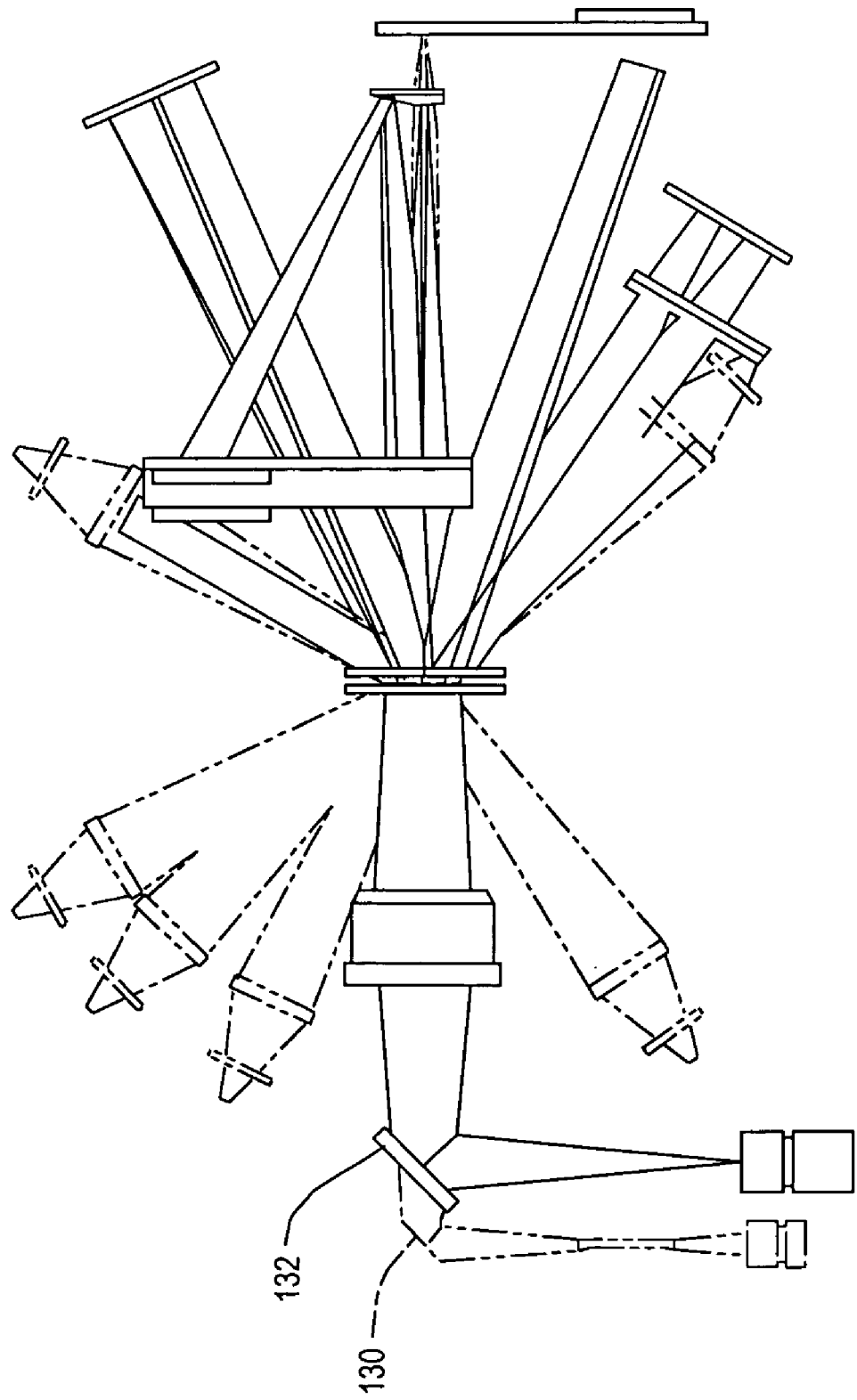
FIG. 9 is an elevation diagram of an illustrative particle size measurement instrument according to the invention that employs two wavelengths.

Referring to FIGS. 8 and 9, the scheme as described above can be further enhanced to allow measurement of more than one wavelength of light. In the preferred embodiment the main focused beam is nominally a 658 nm from a laser diode, with a violet LED at 403 nm. The light from the LED should be masked and conditioned to provide similar (or slightly smaller) numerical aperture to the red laser beam and can be reflected off or its own dichroic mirror 120, 130. This light can pass through the dichroic mirror used to reflect and split the red beam 122, 132. It should be aligned to the optical axis of the red beam in order to allow the use of the same detectors.

The beam quality from the violet LED is generally not good enough to allow the transmission to be measured in the same way as for the red laser, so in the preferred embodiment, the reflective coating on the expanding lens is short-pass dichroic, to allow the violet light to pass through. The back surface of the expanding lens has a form so as to focus the light onto the centre of the detector plane.

Other wavelength ranges could of course be used. The red source could be replaced with a near-infrared source, for example, and the violet source could be replaced with a blue or near-ultraviolet source. These substitutions can improve the dynamic range of the instrument, but they may also introduce additional problems, such as requiring more expensive optical materials. In some embodiments, a tunable or dual-wavelength source could be used.

The sources need not be truly monochromatic, but they should preferably be spatially coherent in that they allow scatter from the larger particles to be differentiated from the focused beam. Laser diodes and LEDs are currently used, but other types of sources could be used, such as sodium lamps, mercury arc lamps, or other types of laser.

Where multiple sources are used, they do not need to be coupled to the apparatus with the mirror arrangement shown in FIGS. 8 and 9. A single mirror could be shared, for example, with sources being turned on and off in succession. The sources could also be coupled into the system by placing one or more of them in alignment with the main optical axis of the system, although this could extend the length of the instrument. The sources could also be driven by known modulation methods.

Figure 10:
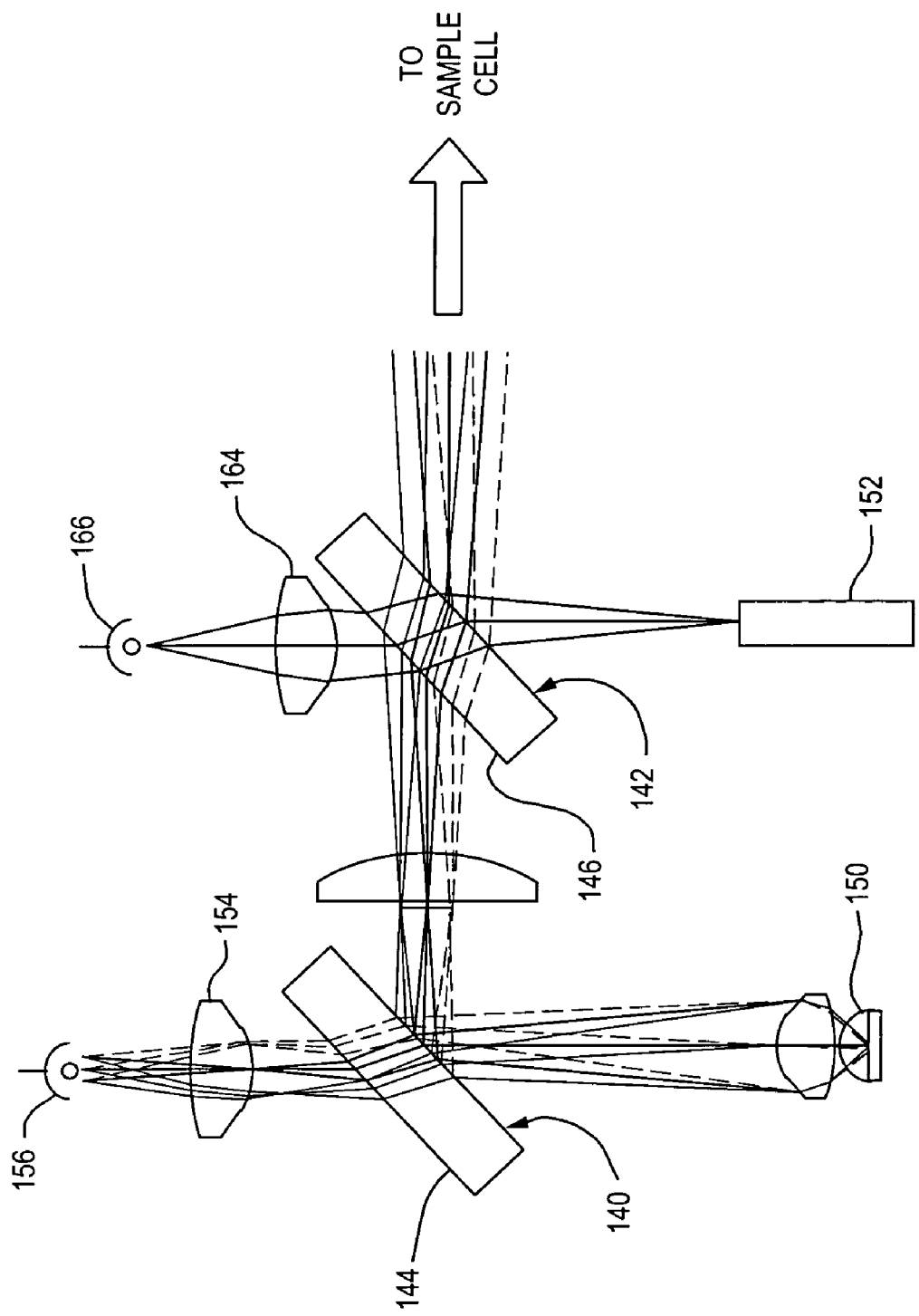
FIG. 10 is a diagram that generally illustrates the dual-wavelength approach presented in connection with FIGS. 8 and 9.
Figure 11:
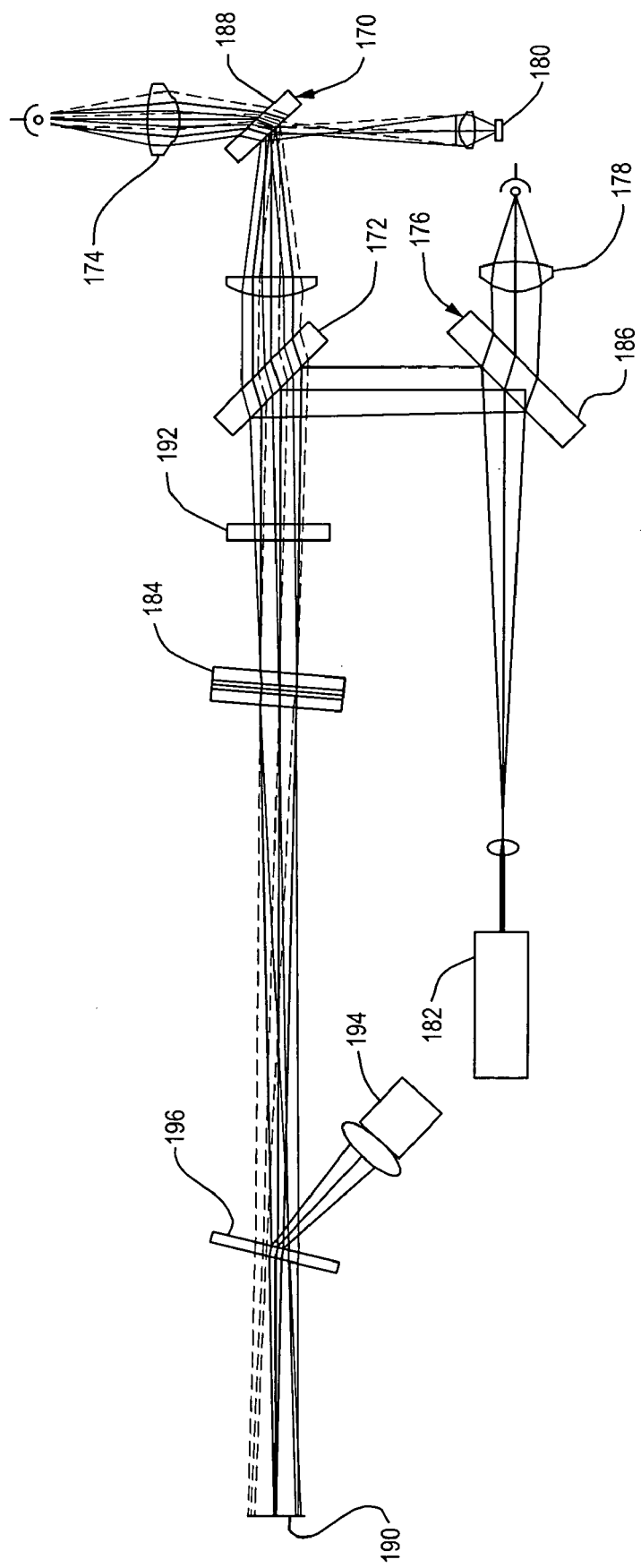
FIG. 11 is a diagram that illustrates the dual-wavelength approach presented in connection with FIGS. 8 and 9 with red sampling being carried out on a separate fold mirror.

Referring to FIGS. 10 and 11, the use of more than one source can also be applied to instruments that employ a conventional geometry. Providing two illumination sources that are coaxial allows the same detectors to be used to detect scattering at the different wavelengths. This is an improvement over some prior art systems that employ illumination beams at different angles, because the full range of the detectors can be exploited.

The use of at least one dichroic mirror is currently preferred, but other approaches for combining beams could also be employed, such as the use of polarized beams, polka dot mirrors, or semi-silvered mirrors. There is also an advantage of allowing red monitoring and enabling glass surfaces to be minimized in diffraction systems due to surface imperfections.

The transmitted second wavelength (i.e. blue) light can either be measured by (i) some of the inner channels of the focal plane detector, or (ii) by a separate detector 194, after being reflected by a second, red-pass dichroic mirror 196 as shown in FIG. 11. An advantage of this approach is that it is an effective way of preventing reflections from the diode surface from getting back to the cell and contaminating the backscatter signals. In addition, where the blue source is an LED, which cannot be collimated as well as a laser, there can be some misalignment or slight angle between the two beams as they follow the same optical axis.

Where a blue laser is used for the second wavelength, the lasers can both be focused and aligned to the same point. A separate alignment mechanism would likely be needed to achieve this, such as through the use of a tip-tilt mechanism on the blue sample mirror 170. In this case they should be coincident at the detector plane to within a few microns (equivalent to what is achieved for the red beam) and coincident at the cell to one or two millimetres or better. The design intent would be to have them perfectly coaxial.

The dichroic mirror 196 close to the focal plane detector will prevent blue light from being collected on the focal plane detector 190 but will not interfere with the red light. It is situated so as to allow larger angles (i.e. angles substantially above the collimation limitation of the blue light source) to get to the same detectors as intended to measure scattered red light. For example, in one embodiment there are 15 "sidescatter" detector elements situated to one side of the focal plane, and these will be able to collect scattering angles from 6 to 60 degrees for both wavelengths. The focal plane detector elements will gather only red light. The low angle blue light will be collected by the blue transmission monitor 194.

The instrument can also use a tilted focal plane detector 190 without the dichroic mirror 196 and transmission monitor 194. If this configuration is used it may be necessary to ensure that reflections from the focal plane are not reflected back to the cell, by means such as tilting the focal plane detector by a small angle.

The detectors can be organized as arrays of elements and/or as separate individual detectors. As is well known, it is preferable to organize them according to a substantially logarithmic progression, with some overlap in the angular ranges of the detectors.

The sample can be presented to the instrument in a variety of ways, but the depth of the sample needs to be constrained to maintain instrument precision. To this end, a sample cell that has at least two walls at least generally normal to the optical axis is preferable. Further walls can also be provided to keep sample materials from contaminating the instrument.

An instrument constructed according to this invention will generally need to maintain alignment and focus under a range of different environmental conditions and sample presentation arrangements. Rather than the conventional scheme of moving the focal plane photo-detector array, this optical scheme allows for realignment to be achieved by moving the expanding optic in the two axes perpendicular to the optical axis whilst keeping the focal plane array fixed relative to the other parts of the instrument. The amount of movement required of this lens is smaller (by a factor similar to the telescopic ratio) than the movement that would be required to move the focal plane array to correct the same misalignment. This allows the expected range of movements to be effected by simple micromanipulators rather than by more cumbersome mechanisms required to move the focal plane detection electronics.

Focus correction can similarly be achieved by small movements of the expanding optic along the optical axis, with an equivalent beneficial reduction in the range and complexity of motion required. Movement of the optic can be performed before each measurement to optimize the pattern of light received by the detector elements for particular conditions. Any method that could be used to move the detector array can be used to move the expanding optic. Such methods can include the use of different types of actuators, such as piezo-electric actuators.

Table 1 is a table of reference designators for the figures.

TABLE 1

Figure 1:
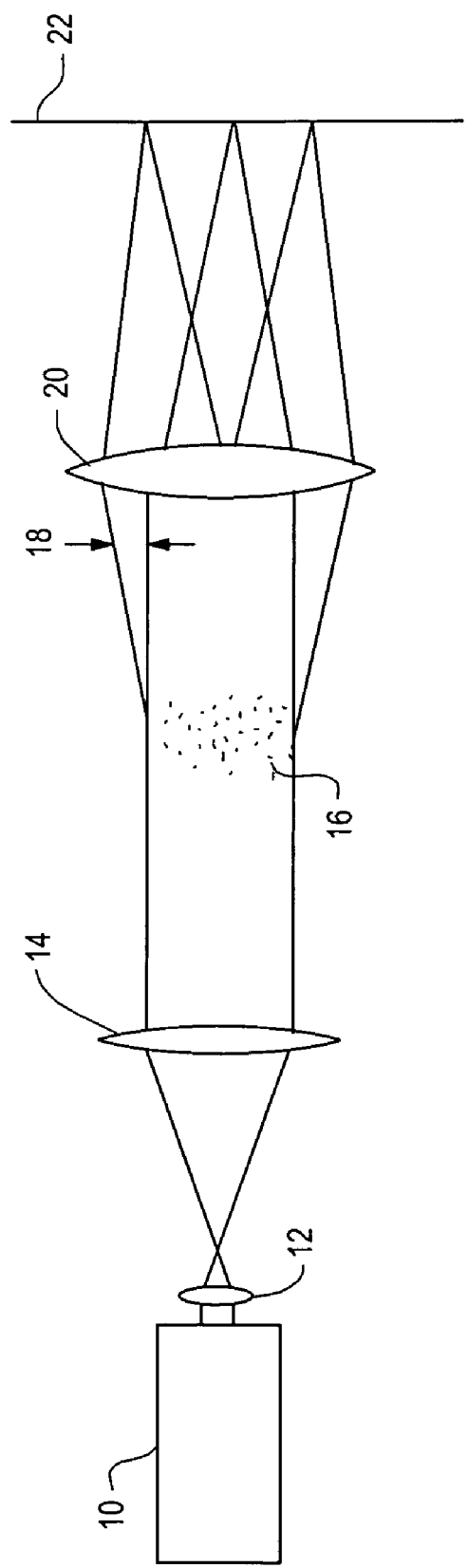
FIG. 1 is a diagram that schematically illustrates a prior art particle measurement instrument that employs a Fourier configuration.

| Figure | Ref. | Description |
|---|---|---|
| FIG. 1 | 10 | 1 mW He/Ne Laser |
| | 12 | Beam Expander |
| | 14 | Parallel Monochromatic Light, such as from a collimating lens |
| | 16 | Particle Field |
| | 18 | −11° For 1 μm Particles |
| | 20 | Fourier Transform Lens |

TABLE 1-continued

Figure 2:
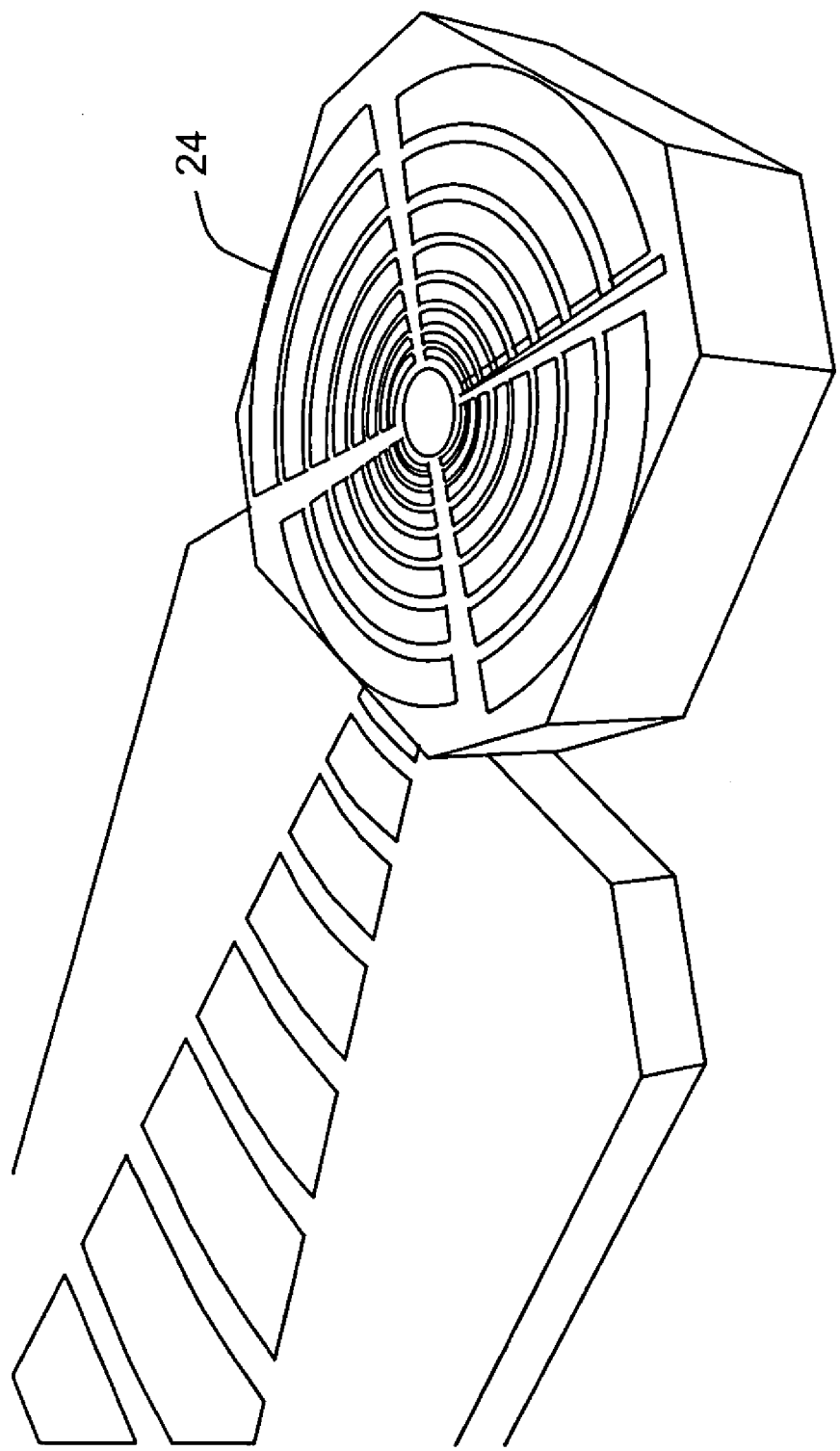
FIG. 2 is a perspective diagram of a prior art set of segmented detector arrays.
Figure 3:
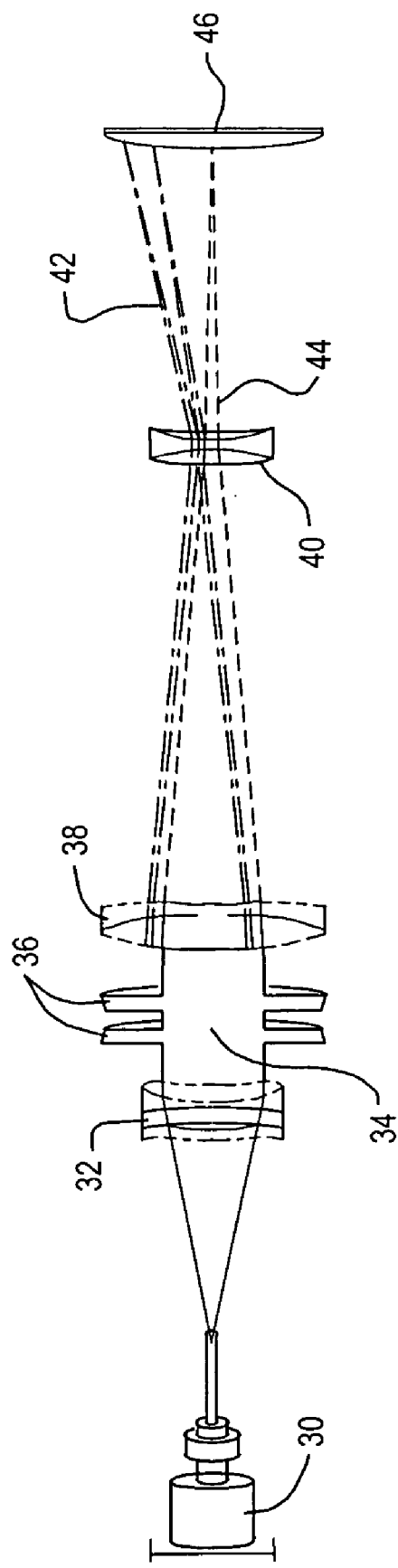
FIG. 3 is a diagram that schematically illustrates a prior art instrument with low angle detection capabilities that uses a telephoto receiving lens configuration.
Figure 4:
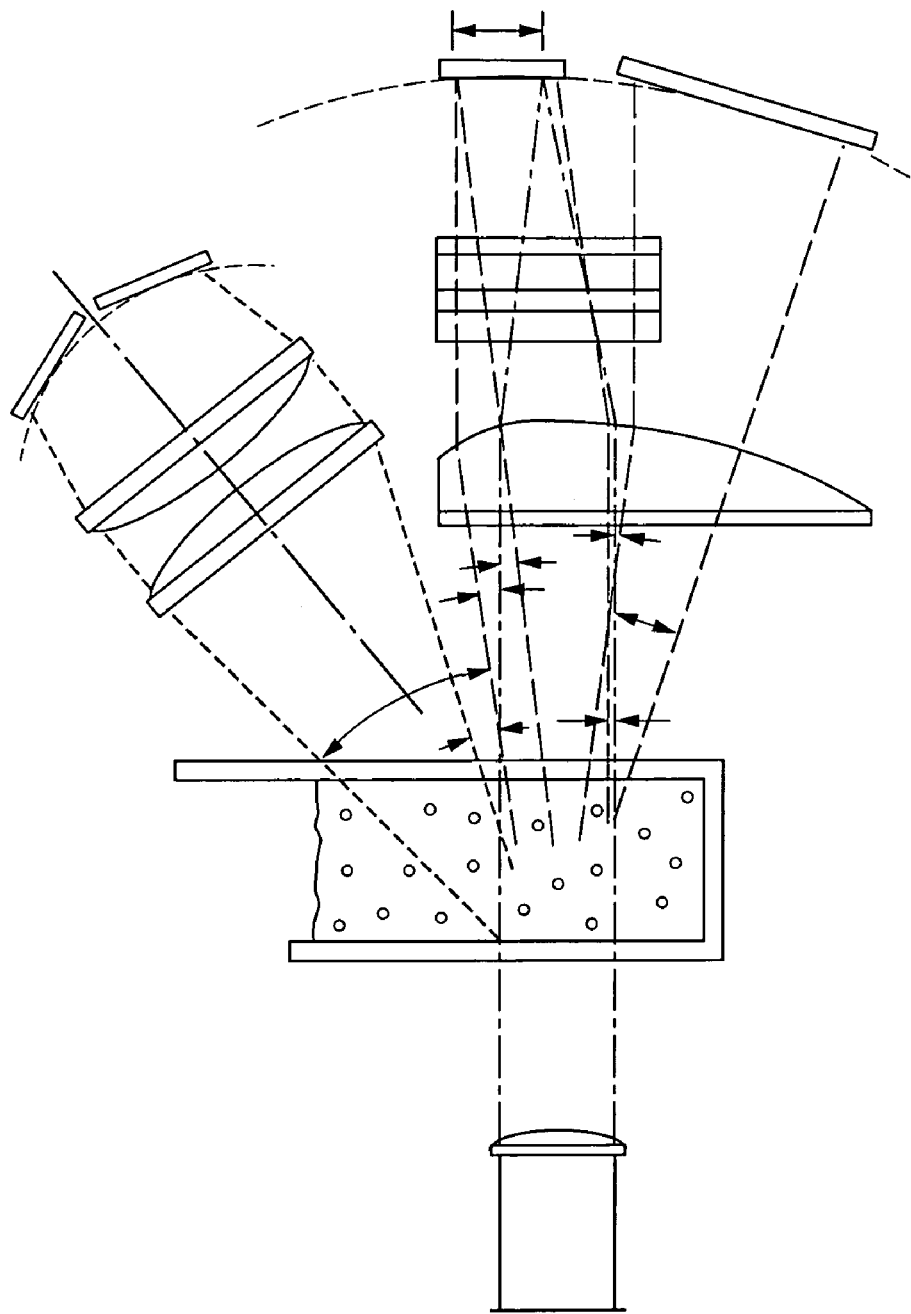
FIG. 4 is a diagram that schematically illustrates a prior art instrument with coulter binocular optics.
Figure 5:
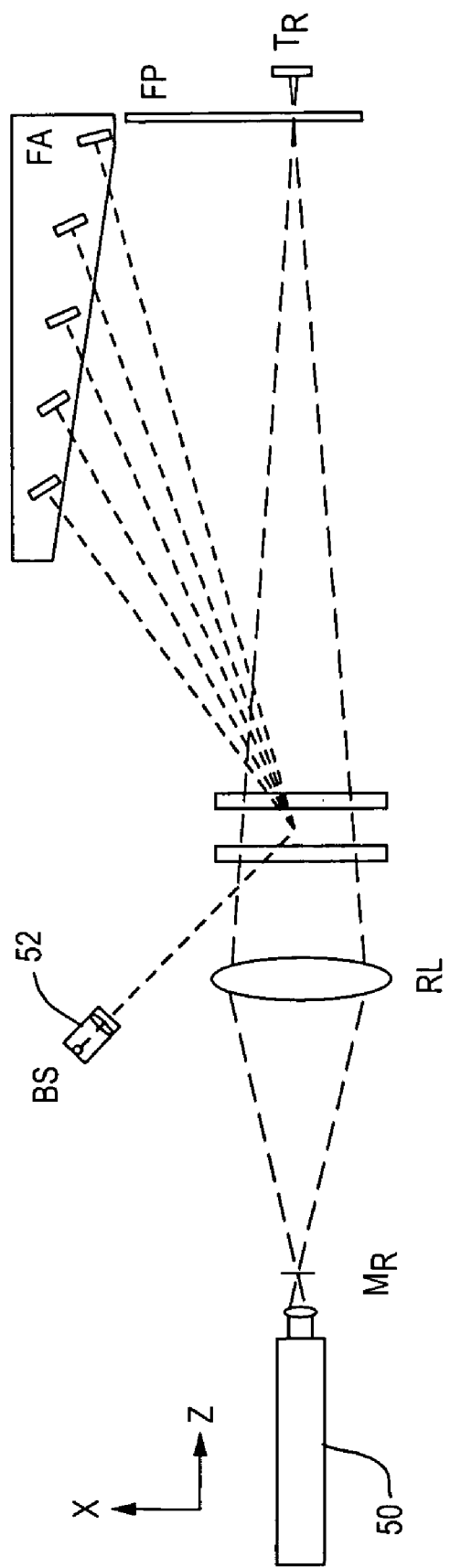
FIG. 5 is a diagram that schematically illustrates a prior art instrument with a reverse Fourier optics configuration.

| Figure | Ref. | Description |
|---|---|---|
| | 22 | Detector in Focal Plane of Lens |
| FIG. 2 | 24 | Segmented Photodetector Array |
| FIG. 3 | 30 | Laser Source |
| | 32 | Collimating Lens |
| | 34 | Sample |
| | 36 | Cell Windows |
| | 38 | Focusing Lens |
| | 40 | Expanding Lens |
| | 42 | Large Angle Scatter (Small Particles) |
| | 44 | Low Angle Scatter (Large Particles) |
| | 46 | Planar Detector Array |
| FIG. 5 | 50 | Laser |
| | 52 | Backscatter Detector |
| FIG. 6 | 70 | Planar Mirror |
| | 72 | Focusing Lens System |
| | 74 | Flow Cell |
| | 76 | Diverging Lens |
| | 78 | Photodetector Array |
| | 80 | Optical Axis |
| FIG. 7 | 70 | Blue-Pass Dichroic Mirror |
| | 72 | Focusing Lens System |
| | 90 | Diode Source Red Laser |
| | 92 | Backscatter Detectors |
| | 94 | Backscatter Detector |
| | 96 | Flow Cell |
| | 98 | Focal Plane Detector Low Angle |
| | 100 | Sidescatter Detector |
| | 102 | Low Numerical Aperture Beam |
| | 104 | High Numerical Aperture Beam |
| | 106 | Focal Plane Detector High Angle |
| | 108 | Truncated Tilted Convex Mirror |
| | 110 | Low Angle Scattered Light |
| FIG. 8 | 120 | Violet Dichroic Mirror |
| | 122 | Red Dichroic Mirror |
| FIG. 9 | 130 | Violet Dichroic Mirror |
| | 132 | Red Dichroic Mirror |
| FIG. 10 | 140 | Blue Sample Mirror |
| | 142 | Dichroic Mirror |
| | 144 | Antireflective Coating (blue) |
| | 146 | Antireflective Coating (red) |
| | 150 | Blue or Violet LED |
| | 152 | Laser (red) |
| | 154 | Light Gathering Lens |
| | 156 | Detector |
| | 164 | Light Gathering Lens |
| | 166 | Detector |
| FIG. 11 | 170 | Blue Sample Mirror |
| | 172 | Red-Pass Dichroic Mirror |
| | 174 | Light Gathering Lens |
| | 176 | Red Sample Mirror |
| | 178 | Light Gathering Lens |
| | 184 | Sample Cell |
| | 186 | Antireflective Coating |
| | 188 | Antireflective Coating |
| | 190 | Focal Plane Detector |
| | 192 | Main Focussing Lens |
| | 194 | Blue Transmission Monitor |
| | 196 | Dichroic (Reflects Blue Light) |

The present invention has now been described in connection with a number of specific embodiments thereof. However, numerous modifications which are contemplated as falling within the scope of the present invention should now be apparent to those skilled in the art. It is therefore intended that the scope of the present invention be limited only by the scope of the claims appended hereto. In addition, the order of presentation of the claims should not be construed to limit the scope of any particular term in the claims.

What is claimed is:

1. A particle characterization instrument, comprising:
a first spatially coherent light source having a beam output aligned with an optical axis,
a focusing optic positioned along the optical axis after the light source,
a sample cell positioned along the optical axis after the focusing optic,
a diverging optic positioned along the optical axis after the sample cell, wherein the diverging optic includes a convex reflective surface,
a first detector positioned outside of the optical axis to receive scattered light within a first range of scattering angles from the diverging optic.

2. The instrument of claim 1 further including a second light source having a wavelength that is different from a wavelength of the first light source.

3. The instrument of claim 2 wherein the wavelength of the first source is longer than the wavelength of the second source, and wherein the different wavelengths provide an increased dynamic range to the instrument.

4. The instrument of claim 3 wherein the first wavelength is a wavelength in the spectral vicinity of red and the second wavelength is a wavelength in the spectral vicinity of violet.

5. The instrument of claim 1 further including a second detector positioned outside the optical axis to receive further scattered light within a second range of scattering angles that are sufficiently large to cause it to pass outside of the diverging optic.

6. The instrument of claim 1 wherein the reflecting surface is a reflecting portion of a circular convex surface and wherein a portion of the circular convex surface is truncated to allow scattered light to pass through unreflected.

7. The instrument of claim 6 further including a second detector positioned outside the optical axis to receive further scattered light within a second range of scattering angles after it passes through the truncated portion of the circular convex surface.

8. The instrument of claim 7 further including a third detector positioned outside the optical axis to receive further scattered light within a third range of scattering angles that are sufficiently large to cause it to pass outside of the diverging optic.

9. The instrument of claim 8 further including a second light source having a wavelength that is different from a wavelength of the first light source.

10. The instrument of claim 1 further including a second light source having a wavelength that is different from a wavelength of the first light source, wherein the divergent optic is dichroic to reflect light from the first source while allowing light from the second source to pass through, and further including a second detector behind the divergent optic to receive scattered light from the second source.

11. The instrument of claim 10 further including a third detector positioned outside the optical axis to receive further scattered light from the second wavelength within a third range of scattering angles that are sufficiently large to pass outside of the diverging optic.

12. The instrument of claim 1 further including a mirror between the light source and the focusing optic that bends the optical axis.

13. The instrument of claim 12 further including a second light source having a wavelength that is different from a wavelength of the first light source, and wherein the mirror is dichroic to reflect light from the first source while allowing light from the second source to pass through.

14. The instrument of claim 13 wherein the first wavelength is a red wavelength and the second wavelength is a violet wavelength.

15. The instrument of claim 1 wherein the source is a solid-state source.

16. The instrument of claim 1 further including at least one backscatter detector positioned outside of the optical axis behind the sample cell.

17. The instrument of claim 1 further including a second light source having a wavelength that is different from a wavelength of the first light source.

18. The instrument of claim 1 further including a second detector positioned outside the optical axis to receive further scattered light within a second range of scattering angles that are sufficiently large to cause it to pass outside of the diverging optic.

19. The instrument of claim 18 wherein the first and second detectors are multi-element detectors.

20. The instrument of claim 1 further including at least one actuator operative to move the diverging optic.

21. The instrument of claim 1 wherein the actuator is operative to move the diverging optic along its optical axis to adjust focus.

22. The instrument of claim 1 wherein the actuator is operative to move the diverging optic perpendicular to its optical axis to adjust alignment.

23. A particle characterization method, comprising:
shining a beam of spatially coherent light,
focusing the beam of light to produce a focused beam of light,
causing the focused beam of light to interact with a plurality of particles to produce scattered light,
spreading at least a portion of the scattered light resulting from the interaction between the focused beam and the particles with a convex reflective surface to produce a spread scattered light beam, and
detecting at least part of the spread scattered light beam.

24. A particle characterization instrument, comprising:
means for shining a beam of spatially coherent light,
means for focusing the beam of light to produce a focused beam of light,
means for causing the focused beam of light to interact with a constrained plurality of particles to produce scattered light,
convex reflective means for spreading at least a portion of the scattered light resulting from the interaction between the focused beam and the particles to produce a spread scattered light beam, and
means for detecting at least part of the spread scattered light beam.

25. The instrument of claim 1,
wherein the first spatially coherent light source is a first spatially coherent light source having a first wavelength and wherein its beam output is a first beam output,
further including a second light source having a second wavelength that is different from the first wavelength and having a second beam output,
further including a first optical combiner responsive to the first beam output and to the second beam output and being positioned to direct at least a portion of a first output beam from the first beam output and at least a portion of a second output beam from the second beam output along the optical axis,
wherein the sample cell is positioned along the optical axis such that it can receive the first output beam or the second output beam as they are the directed along the same optical axis, and
wherein the first detector is positioned outside of the optical axis to receive scattered light from the sample cell resulting from interaction between the sample and either the first output beam or the second outlet beam.

26. The instrument of claim 25 wherein the optical combiner is a dichroic mirror.

27. The instrument of claim 26, further including another mirror, and wherein the dichroic mirror redirects at least a portion of the first output beam along the optical axis and the other mirror redirects at least a portion of the second output beam along the optical axis.

28. The instrument of claim 27 further including a first detector positioned to receive at least a portion of the first output beam and a second detector positioned to receive at least a portion of the second output beam.

29. The instrument of claim 25 wherein the optical combiner is positioned to allow full overlap of the beams.

30. The instrument of claim 25 wherein the second light source is a spatially coherent light source.

31. The method of claim 23, wherein the step of shining a beam shines a beam of spatially coherent light having a first wavelength and wherein the beam is a first beam, and further including:
shining a second beam of light having a second wavelength,
directing at least one of the first and second beams of light to cause them to shine along a same optical axis,
causing the second directed beam of light to interact with the sample in the optical axis to produce more scattered light, and
detecting at least part of the scattered light from the second beam.

32. The method of claim 31 wherein the step of directing is a two-part step that redirects the first and second beams of light.

33. The method of claim 31 wherein the step of shining a second beam of light shines spatially coherent light.

34. The method of claim 31 wherein the step of shining a first beam and the step of detecting at least part of the scattered light from the first beam occur before the step of shining a second beam.

35. The instrument of claim 24,
wherein the means for shining is for shining a beam of spatially coherent light having a first wavelength and wherein the beam is a first beam,
further including means for shining a second beam of light having a second wavelength,
further including means for directing at least one of the first and second beams of light to cause them to shine along a same optical axis,
wherein the means for causing is for causing the first directed beam of light to interact with a sample including a plurality of particles in the optical axis to produce scattered light, and for causing the second directed beam of light to interact with the sample in the optical axis to produce more scattered light, and
wherein the means for detecting is for detecting the scattered light from the first beam and the second beam.

* * * * *